(12) United States Patent
Shroff et al.

(10) Patent No.: US 7,297,798 B2
(45) Date of Patent: Nov. 20, 2007

(54) PROCESS FOR THE PREPARATION OF THE INSECTICIDE IMIDACLOPRID

(75) Inventors: Dipesh K. Shroff, Mumbai (IN); Ashok K. Jain, Mumbai (IN); Rajendra P. Chaudhari, Mumbai (IN); Raghuvirsinh B. Jadeja, Mumbai (IN); Mahendrasinh S. Gohil, Mumbai (IN)

(73) Assignee: Excel Crop Care Limited, Mumbai (IN)

( * ) Notice: Subject to any disclaimer, the term of this patent is extended or adjusted under 35 U.S.C. 154(b) by 80 days.

(21) Appl. No.: 11/349,461

(22) Filed: Feb. 7, 2006

(65) Prior Publication Data

US 2007/0197792 A1    Aug. 23, 2007

(51) Int. Cl.
*C07D 401/06* (2006.01)

(52) U.S. Cl. .................................................. 546/274.7

(58) Field of Classification Search .............. 546/274.7
See application file for complete search history.

(56) References Cited

U.S. PATENT DOCUMENTS 6,307,053 B1    10/2001    Yeh et al.
6,818,769 B2 *  11/2004    Chen ........................... 544/331

FOREIGN PATENT DOCUMENTS

IN          181755       9/1998

\* cited by examiner

*Primary Examiner*—Kamal A. Saeed
(74) *Attorney, Agent, or Firm*—Klein, O'Neill & Singh, LLP; Howard J. Klein

(57) ABSTRACT

A process for the preparation of the insecticide imidacloprid includes the reaction of 2-chloro-5-chloromethyl pyridine with 2-nitroiminoimidazolidine, carried out in the molar ratio of 1:1 to 1:1.2, in the presence of an alkali metal hydroxide in an aprotic solvent at 45 to 60° C. under stirring.

6 Claims, No Drawings

PROCESS FOR THE PREPARATION OF THE INSECTICIDE IMIDACLOPRID

CROSS-REFERENCE TO RELATED APPLICATION

Not Applicable

FEDERALLY SPONSORED RESEARCH OR DEVELOPMENT

Not Applicable

BACKGROUND OF THE INVENTION

1. Field of the Invention

This invention relates to a process for the preparation of the insecticide imidacloprid.

2. Prior Art

Imidacloprid, namely, 1-(6-chloro-3-pyridylmethyl)-N-nitroimidazolidin-2-ylideneamine, is a systemic, chloro-nicotinyl insecticide with soil, seed and foliar uses for the control of sucking insects including rice hoppers, aphids, thrips, whiteflies, termites, turf insects, soil insects and beetles. It is most commonly used on rice, cereals, maize, potatoes, vegetables, sugar beets, fruits, cotton, hops or turfs, and is especially systemic when used as a seed or soil treatment.

U.S. Pat. No. 6,307,053 describes a process for the preparation of imidacloprid comprising reacting 2-nitroiminoimidazolidine with 2-chloro-5-chloromethyl pyridine in stoichiometric amounts in the presence of an alkali metal carbonate in an organic solvent under reflux condition. The alkali metal carbonate may be lithium, potassium or sodium carbonate. The organic solvent may be alcohols, ketones, acetonitrile or dimethyl formamide. Due to the alkali metal carbonates being not very soluble in the organic solvents, the solutions of the alkali carbonates are not easily flowable and pumpable, and the reaction mixture is not very homogenous so as to be easily stirred. Therefore, the above process is difficult to carry out. Besides, the filtrate containing imidacloprid obtained by the above process is concentrated by vacuum distillation. Due to the presence of unreacted alkali metal carbonates and their related salts in the filtrate resulting from use of alkali carbonates, there is bumping (flashing) turbulence during vacuum distillation of the filtrate, thereby rendering the process more difficult to carry out. Also, alkali metal carbonates have low basisity, thereby increasing the reaction time. The above process is described to be an improvement over the process of employing sodium hydride (NaH) in the place of alkali metal carbonate. Sodium hydride is a very hazardous reagent. Therefore, handling of the sodium hydride-based reaction is very difficult and cumbersome.

Indian Patent No 181755 describes a process for the preparation of imidacloprid comprising, among other steps, condensation of 3-chloromethyl-6-chloropyridine with 2-nitroimino-1,3-dihydro imidazole in the presence of inorganic bases and ketonic solvents. The inorganic bases used may be carbonates or bicarbonates of sodium or potassium. The solvents may be acetone, methyl butyl ketone, methyl-t-butylketone or acetonitrile. The problems associated with the use of alkali carbonates in the above-referenced U.S. Pat. No. 6,307,053 are encountered in this process also.

SUMMARY OF THE INVENTION

An object of the invention is to provide a process for the preparation of the insecticide imidacloprid that is very easy to carry out.

Another object of the invention is to provide a process for the preparation of the insecticide imidacloprid that gives a good yield and that is economical.

Another object of the invention is to provide a process for the preparation of the insecticide imidacloprid that reduces the reaction time.

Another object of the invention is to provide a process for the preparation of the insecticide imidacloprid that eliminates hazardous reagents and that is safer to carry out.

DETAILED DESCRIPTION OF THE INVENTION

According to the invention, there is provided a process for the preparation of the insecticide imidacloprid comprising reacting 2-chloro-5-chloromethyl pyridine with 2-nitroiminoimidazolidine with in the molar ratio 1:1 to 1:1.2 in the presence of an alkali metal hydroxide in an aprotic solvent at 45 to 60° C. under stirring.

It has been surprisingly found that the yield of imidacloprid is improved if the molar proportion of the 2-nitroiminoimidazolidine is marginally higher than that of 2-chloro-5-chloromethyl pyridine. Preferably, the reaction of 2-chloro-5-chloromethyl pyridine with 2-nitroiminoimidazolidine is carried out in the molar ratio 1:1.12 so as to improve the yield of imidacloprid.

The alkali metal hydroxide may be potassium hydroxide or sodium hydroxide, preferably sodium hydroxide.

The aprotic solvent may be dimethyl formamide or N,N-dimethyl acetamide, preferably dimethylformamide.

Preferably, the reaction of 2-chloro-5-chloromethyl pyridine with 2-nitroiminoimidazolidine is carried out at 50° C., so as to obtain good yields of imidacloprid.

It has also been surprisingly found that the yield of imidacloprid is improved if the alkali hydroxide is added in two lots, one after the other.

According to the invention, alkali metal hydroxides are employed in the reaction thereof, which have improved solubility in the aprotic solvents. Therefore, flowability and pumpability of the solutions of the alkali hydroxides are improved. Also, homogeneity of the reaction mixture is improved so as to be easily stirred. Therefore, it is easy to carry out the process of the invention. According to the invention, the use of alkali metal carbonates in the reaction is eliminated, and thus the resulting problems from unreacted alkali metal carbonates and their related salts in the filtrate are avoided. The alkali metal hydroxides used in the present invention have improved reactivity and basisity, because of which reaction time is reduced, and the amount of unreacted alkali metal hydroxides in the filtrate is likewise reduced. Therefore, bumping (flashing) turbulence during vacuum distillation of the filtrate is avoided, thereby rendering the process easier to be carried out. The invention eliminates the use of the hazardous reagent sodium hydride, and it is, therefore, safer to carry out. According to the invention, the yield of imidacloprid is good, thereby rendering the process economical.

The following experimental examples are illustrative of the invention, but not limitative of the scope thereof.

EXAMPLE 1

Sodium hydroxide (6 gm) was added to 2-nitroiminoimidazolidine (16 gm, 0.123 moles) in dimethylformamide (50 ml). The temperature of the reaction mixture was brought down to 50° C. in a water bath. A solution of 2-chloro-5-chloromethyl pyridine (20 gm, 0.123 moles) in dimethylformamide (100 ml) was added to the reaction mixture in 4 hours. The reaction mixture was cooked for another 4 hours at the same temperature. The reaction mixture was stirred throughout. On completion, the reaction mixture was filtered. The residue contained sodium chloride (7 gm). The filtrate was concentrated by vacuum distillation and poured into distilled water (100 ml). The pH of the solution was adjusted to 4, using dilute hydrochloric acid to precipitate out imidacloprid, which was filtered out and washed with methanol (90 ml). The yield was 23 gm, 76.6% with 94.16% purity.

EXAMPLE 2

Sodium hydroxide (6 gm) was added to 2-nitroiminoimidazolidine (18 gm, 0.138 moles) in dimethylformamide (50 ml). The temperature of the reaction mixture was brought down to 50° C. in a water bath. A solution of 2-chloro-5-chloromethyl pyridine (20 gm, 0.123 moles) in dimethylformamide (100 ml) was added to the reaction mixture in 4 hours. The reaction mixture was cooked for another 4 hours at the same temperature. The reaction mixture was stirred throughout. On completion, the reaction mixture was filtered. The residue contained sodium chloride (6.45 gm). The filtrate was concentrated by vacuum distillation and poured into distilled water (100 ml). The pH of the solution was adjusted to 4, using dilute hydrochloric acid to precipitate out imidacloprid, which was filtered out and washed with methanol (90 ml). The yield was 20 gm, 66.6% with 95.18% purity.

EXAMPLE 3

Sodium hydroxide (3 gm) was added to 2-nitroiminoimidazolidine (18 gm, 0.138 moles) in dimethylformamide (50 ml). The temperature of the reaction mixture was brought down to 50° C. in a water bath. A solution of 2-chloro-5-chloromethyl pyridine (20 gm, 0.123 moles) in dimethylformamide (100 ml) was added to the reaction mixture in 4 hours. Sodium hydroxide (3 gm) was also added to the reaction mixture after half the solution of 2-chloro-5-chloromethyl pyridine was added to it. The reaction mixture was cooked for another 4 hours at the same temperature. The reaction mixture was stirred throughout. On completion, the reaction mixture was filtered. The residue contained sodium chloride (7.4 gm). The filtrate was concentrated by vacuum distillation and poured into distilled water (100 ml). The pH of the solution was adjusted to 4, using dilute hydrochloric acid to precipitate out imidacloprid, which was filtered out and washed with methanol (90 ml). The yield was 23.5 gm, 78.3% with 96.2% purity.

We claim:

1. A process for the preparation of the insecticide imidacloprid, comprising reacting 2-chloro-5-chloromethyl pyridine with 2-nitroiminoimidazolidine in a molar ratio 1:1 to 1:1.2 in the presence of an alkali metal hydroxide in an aprotic solvent at 45 to 60° C. under stirring.

2. A process as claimed in claim 1, wherein the reaction of 2-chloro-5-chloromethyl pyridine with 2-nitroiminoimidazolidine is carried out in a molar ratio 1:1.12.

3. A process as claimed in either of claims 1 or 2, wherein the alkali metal hydroxide is sodium hydroxide.

4. A process as claimed in either of claims 1 or 2, wherein the aprotic solvent is dimethylformamide.

5. A process as claimed in either of claims 1 or 2, wherein the reaction of 2-chloro-5-chloromethyl pyridine with 2-nitroiminoimidazolidine is carried out at 50° C.

6. A process as claimed in either of claims 1 or 2, wherein the alkali metal hydroxide is added in two lots, one after the other.

* * * * *